(12) United States Patent
Yi et al.

(10) Patent No.: US 11,468,577 B2
(45) Date of Patent: Oct. 11, 2022

(54) DEVICE FOR PROVIDING 3D IMAGE REGISTRATION AND METHOD THEREFOR

(71) Applicant: GMEDITEC CORP., Incheon (KR)

(72) Inventors: Won-Jin Yi, Seoul (KR); Sangjeong Lee, Seoul (KR); Min-Hyuk Choi, Seoul (KR)

(73) Assignee: GMEDITEC CORP., Namdong-gu (KR)

( * ) Notice: Subject to any disclaimer, the term of this patent is extended or adjusted under 35 U.S.C. 154(b) by 0 days.

(21) Appl. No.: 17/264,921

(22) PCT Filed: Oct. 22, 2018

(86) PCT No.: PCT/KR2018/012472
§ 371 (c)(1),
(2) Date: Feb. 1, 2021

(87) PCT Pub. No.: WO2020/027377
PCT Pub. Date: Feb. 6, 2020

(65) Prior Publication Data
US 2021/0304423 A1    Sep. 30, 2021

(30) Foreign Application Priority Data

Jul. 31, 2018   (KR) .................. 10-2018-0089310

(51) Int. Cl.
*G06T 7/33* (2017.01)
*A61B 34/20* (2016.01)
(Continued)

(52) U.S. Cl.
CPC .............. *G06T 7/33* (2017.01); *A61B 34/20* (2016.02); *G06T 7/593* (2017.01); *H04N 13/204* (2018.05);
(Continued)

(58) Field of Classification Search
CPC . G06T 7/33; G06T 7/593; G06T 2207/10024; G06T 2207/10028;
(Continued)

(56) References Cited

U.S. PATENT DOCUMENTS

| | | | | |
|---|---|---|---|---|
| 5,999,840 A | * | 12/1999 | Grimson | G16H 30/20 606/130 |
| 8,363,228 B2 | * | 1/2013 | Babayoff | G01J 3/02 250/559.49 |

(Continued)

FOREIGN PATENT DOCUMENTS

| | | |
|---|---|---|
| JP | 2016107059 | 6/2016 |
| KR | 20140067526 | 6/2014 |

(Continued)

OTHER PUBLICATIONS

Choi, et al., On-demand Automatic Registration Method between CT and Electromagnetic Tracking Device Using RGB-D Camera, 2018 The Korean Society of Medical & Biological Engineering Spring Conference, Konkuk University Glocal Campus, AI in Biomedical Engineering: Major Tide in the 4th Industrial Revolution, May 2018.

(Continued)

*Primary Examiner* — Gregory M Desire
(74) *Attorney, Agent, or Firm* — Cantor Colburn LLP

(57) ABSTRACT

A device for providing 3D image registration includes: a collection unit acquiring 3D depth data of a part and an image of a registration body from a depth recognition camera and acquiring three-dimensional coordinates of a positioning tool on the registration body from a positioning device; a first registration unit performing surface registration of a pre-stored 3D medical image of patient and the 3D depth data; a second registration unit extracting camera reference three-dimensional coordinates of a landmark attached to the registration body from the image of the (Continued)

registration body and converting pre-stored relative position information of the landmark with reference to the three-dimensional coordinates of the positioning tool, to perform registration of camera reference three-dimensional coordinates of the landmark and the converted position information thereof; and a third registration unit performing final registration by using results of registration performed by the first registration unit and the second registration unit.

20 Claims, 4 Drawing Sheets

(51) Int. Cl.
 *G06T 7/593* (2017.01)
 *H04N 13/204* (2018.01)
(52) U.S. Cl.
 CPC .............. *A61B 2034/2065* (2016.02); *G06T 2207/10024* (2013.01); *G06T 2207/10028* (2013.01); *G06T 2207/30004* (2013.01)
(58) Field of Classification Search
 CPC ............ G06T 2207/3004; A61B 34/20; A61B 2034/2065; H04N 13/204
 See application file for complete search history.

(56) References Cited

U.S. PATENT DOCUMENTS

| | | | |
|---|---|---|---|
| 10,092,191 B2 * | 10/2018 | Yu | G06T 11/00 |
| 10,832,408 B2 * | 11/2020 | Srimohanarajah | G16H 40/60 |
| 10,918,444 B2 * | 2/2021 | Stopp | A61B 34/20 |
| 2013/0317363 A1 | 11/2013 | Case et al. | |
| 2017/0084036 A1 * | 3/2017 | Pheiffer | A61B 5/061 |
| 2018/0247427 A1 * | 8/2018 | Geiger | G06T 7/73 |

FOREIGN PATENT DOCUMENTS

| | | |
|---|---|---|
| KR | 20150053202 | 5/2015 |
| KR | 20160042297 | 4/2016 |

OTHER PUBLICATIONS

Choi, et al., On-Demand Automatic Registration Method between CT and Electromagnetic Tracking Device Using RGB-D Camera, 40th Annual international Conference of the IEEE Engineering in Medicine and Biology Society, Hawaii Convention Center, Honolulu, Hawaii, Jul. 17-21, 2018.

International Search Report—PCT/KR018/012472 dated Apr. 29, 2019.

* cited by examiner

DEVICE FOR PROVIDING 3D IMAGE REGISTRATION AND METHOD THEREFOR

TECHNICAL FIELD

A device for providing 3D image registration and a method therefor are provided.

BACKGROUND ART

Recently, minimally invasive endoscopic surgery (MIS) is widely used in surgeries of otolaryngology, orthopedics, neurosurgery, laparoscopic, and the like. Since a field of view is limited in these endoscopic surgeries in many cases, it is important to recognize an exact position of an affected area or a structure.

Accordingly, image-guided surgical navigation systems in which a three-dimensional position tracking device is combined with the endoscope are consistently being studied. The image-guided surgical navigation system is advantageous to reduce the surgical risks and improve position control accuracy, convenience, and stability.

In the surgery that utilizes a surgical navigation system using three-dimensional medical images such as MRI, CT, or ultrasound, registration between a patient image coordinate system before surgery and a positioning device coordinate system is essentially requested.

According to a registration method of the related art, feature points used for registration are manually oriented in a patient's image space and a patient's physical space or obtained by scanning a plurality of points in a contact manner. However, according to the manual registration method, when a landmark is acquired, inconvenience is caused to the patient or the operator and depending on the skill level of the technician, a preparation time for surgery is increased or accuracy of the registration is determined. Further, cross-infection between patients may occur when a physical structure is used to be in contact with a portion of the patient to be registered in a contact manner to scan the portion to be registered.

Accordingly, a system which automatically registers and provides a 3D image in real time without making a contact with a skin of the patient is requested.

DISCLOSURE

Technical Problem

An object of one exemplary embodiment of the present invention is to automatically register and provide a positioning device coordinate system and a patient's image coordinate system in real time during the surgery to be utilized for an image-guided surgery process.

In addition to the above objects, an exemplary embodiment of the present invention may be used for implementing other objects that are not mentioned in detail.

Technical Solution

According to an aspect of the present invention, a device for providing 3D image registration includes: a collection unit for acquiring 3D depth data of a part to be registered and an image of a registration body from a depth recognition camera and acquiring three-dimensional coordinates of a positioning tool mounted on the registration body from a positioning device; a first registration unit for performing surface registration of a pre-stored 3D medical image of a patient and the 3D depth data; a second registration unit for extracting camera reference three-dimensional coordinates of a landmark attached to the registration body from the image of the registration body and converting pre-stored relative position information of the landmark with reference to the three-dimensional coordinates of the positioning tool, so as to perform registration of camera reference three-dimensional coordinates of the landmark and the converted position information of the landmark; and a third registration unit for performing final registration by using results of registration performed by the first registration unit and the second registration unit.

The first registration unit may extract a part to be registered from the 3D medical image acquired before surgery as 3D surface data and convert the 3D depth data of the patient collected during the surgery into 3D scan data to perform surface registration between the 3D surface data and the 3D scan data.

The first registration unit may perform surface registration by means of an SAC-IA algorithm to generate surface registration data and apply the surface registration data and the 3D surface data to a precise registration ICP algorithm to generate first registration data in which a 3D medical image coordinate system and a depth recognition camera coordinate system match.

In the registration body, the positioning tool is mounted and the landmark having a different color from the registration body is attached thereto, and a storing unit which stores relative position information of the landmark measured with reference to the positioning tool before surgery is further provided.

The second registration unit may convert pre-stored relative position information of the landmark with reference to the three-dimensional coordinates of the positioning tool collected during the surgery to generate positioning device reference coordinates of the landmark.

The second registration unit may extract a color image of the registration body and 3D depth data of the registration body from the image of the registration body and deduct camera reference three-dimensional coordinates of the landmark by means of a two-dimensional position of the landmark deducted using different color information from the color image and the 3D depth data of the registration body.

The second registration unit may generate second registration data to match the depth recognition camera coordinate system and the positioning device coordinate system by means of one-by-one point-to-point matching between the positioning device reference coordinates of the landmark and the camera reference three-dimensional coordinates of the landmark.

The third registration unit may register the first registration data and the second registration data to match the coordinate system of the 3D medical image and the coordinate system of the positioning device.

The device for providing 3D image registration may further include: a reference tracking coordinate unit which attaches a reference tracking tool to a part of a body of the patient during surgery and converts a coordinate tracked by the positioning device into a reference tracking tool coordinate system.

The third registration unit may convert data obtained by performing final registration into the reference tracking tool coordinate system.

According to an aspect of the present invention, a registration method of a 3D image registration providing device includes acquiring 3D depth data of a part to be registered and an image of a registration body from a depth recognition camera and acquiring three-dimensional coordinates of a positioning tool mounted on the registration body from a positioning device; generating first registration data by performing registration of a 3D medical image of a patient stored in advance before surgery and the 3D depth data; generating second registration data by extracting camera reference three-dimensional coordinates of a landmark attached to the registration body from the image of the registration body and converting pre-stored relative position information of the landmark with reference to the three-dimensional coordinates of the positioning tool, so as to perform registration of camera reference three-dimensional coordinates of the landmark and the converted position information of the landmark; and performing final registration by using the first registration data and the second registration data.

Advantageous Effects

According to an exemplary embodiment of the present invention, the registration body is not directly attached to the skin of the patient so that cross-infection between patients caused when the registration body is attached to the skin may be minimized.

Further, according to an exemplary embodiment of the present disclosure, the registration between 3D images is automatically performed in real time so that it is not affected by a technical skill level of a technician for the 3D image registration. Therefore, a registration result with a high accuracy may be constantly acquired by minimizing errors depending on the difference in skill levels.

Further, according to an exemplary embodiment of the present invention, an overall surgery time is reduced and the precision of the surgery may be improved by image guide.

BEST MODE

Figure 1:
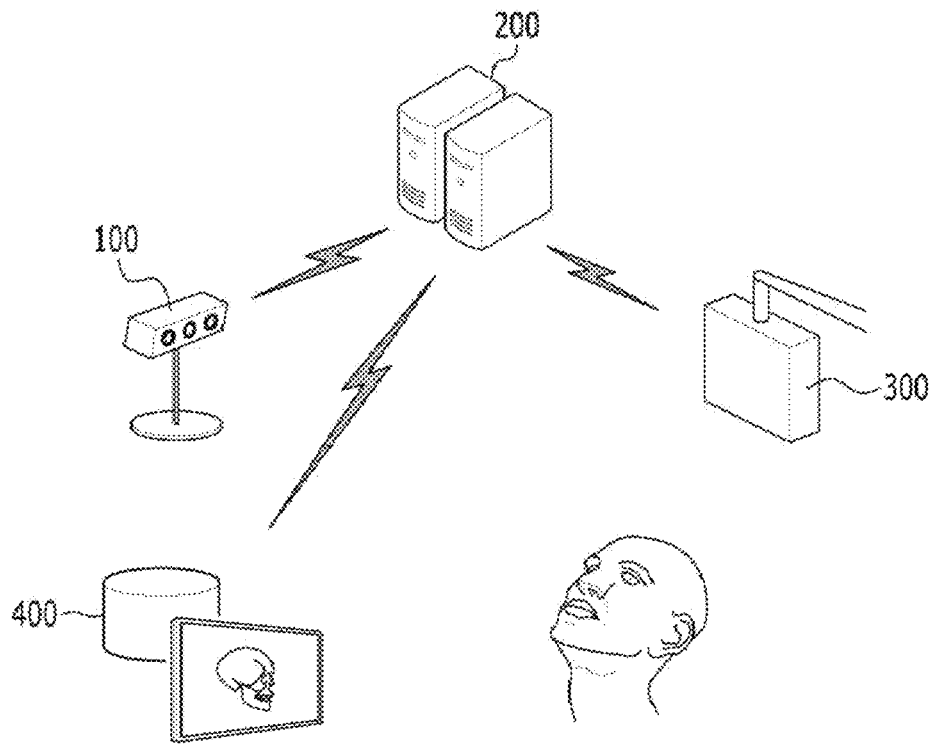
FIG. 1 is a diagram illustrating a 3D image registration providing system according to an exemplary embodiment of the present invention.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification. In addition, the detailed description of the widely known technologies will be omitted.

In the specification, unless explicitly described to the contrary, the word "comprise" and variations such as "comprises" or "comprising", will be understood to imply the inclusion of stated elements but not the exclusion of any other elements.

Hereinafter, a 3D image registration providing system using a depth recognition camera and a positioning device will be described in detail with reference to FIG. 1.

FIG. 1 is a diagram illustrating a 3D image registration providing system according to an exemplary embodiment of the present invention.

As illustrated in FIG. 1, the 3D image registration providing system includes a depth recognition camera 100, a 3D image registration providing device 200, a positioning device 300, and a database 400.

First, the depth recognition camera 100 captures a target to be captured to generate a camera screen of a color image and 3D depth data. Here, the depth recognition camera 100 may include a three-dimensional laser scanner using triangulation, an endoscope device, a depth camera using a structural ray pattern, a time of flight (TOF) type depth camera using a reflection time difference of infrared (IR), a C-arm device, and an optical coherence tomography, but is not limited thereto. The 3D image registration providing device 200 registers and provides images stored in the depth recognition camera 100, the positioning device 300, and the database 400.

When the 3D medical image of the patient is received before the surgery, the 3D image registration providing device 200 extracts a registration portion from the received 3D medical image to generate 3D surface data of the extracted registration portion. The 3D image registration providing device 200 may store 3D surface data corresponding to the 3D medical image of the patient in the database 400.

The 3D image registration providing device 200 receives an image of the depth recognition camera 100 and a three-dimensional coordinate of a positioning tool mounted on a registration body acquired by the positioning device 300 during the surgery. The 3D image registration providing device 200 collects the 3D medical image stored in the database 400 and relative position information of a landmark attached to the registration body.

By doing this, the 3D image registration providing device 200 performs first registration between the 3D medical image and the image of the depth recognition camera 100 and performs second registration between the image of the registration body by means of the depth recognition camera 100 and the landmark coordinate value converted with reference to the three-dimensional coordinate of the positioning device 300.

Finally, the 3D image registration providing device 200 may perform final registration of the first registration data and the second registration data.

In this case, the 3D image registration providing device 200 may selectively collect 3D depth data included in an image received by the depth recognition camera 100 and the color image which is a camera captured screen of the target to be captured. For example, the 3D image registration providing device 200 selectively collects only 3D depth data from the depth recognition camera 100 to register only with the 3D surface image and collects a color image obtained by capturing the registration body by the depth recognition camera 100 and the 3D depth data of the registration body to register with the position coordinate of the landmark. Next, the positioning device 300 generates a 3D position coordinate from an image captured with reference to the positioning device. The positioning device 300 may deduct and provide a position coordinate of a tool with a sensor with reference to the positioning device.

The database 400 stores the 3D medical image of the patient and the coordinate data of the landmark.

Here, the 3D medical image refers to a medical image obtained by capturing a patient using a medical image capturing device such as a computed tomography (CT) device, a magnetic resonance imaging (MRI) device, a positron emission tomography (PET) device, before surgery.

In the meantime, a registration body which is manufactured before surgery is a tool which provides a reference coordinate for registration of the 3D medical image and positioning data and at least three registration landmarks and a positioning tool may be attached thereto.

In other words, when a coordinate of the landmark is extracted with reference to the three-dimensional coordinate of the positioning tool attached to the registration body, the 3D image registration providing device 200 may register a depth recognition camera coordinate system space and a positioning device coordinate system space based on the coordinate of the landmark.

Accordingly, in the database 400, a coordinate of the landmark extracted with reference to the positioning tool of the registration body before surgery is stored.

Here, as the registration landmark, three or more landmarks are attached to the registration body and have different colors from the registration body. Here, the colors of the landmark and the registration body may be set by complementary colors with a large color difference.

Further, the database 400 may store medical treatment details for every patient and may be encrypted and stored to protect personal information of each patient.

Hereinafter, a 3D image registration providing device according to an exemplary embodiment of the present invention will be described in detail.

Figure 2:
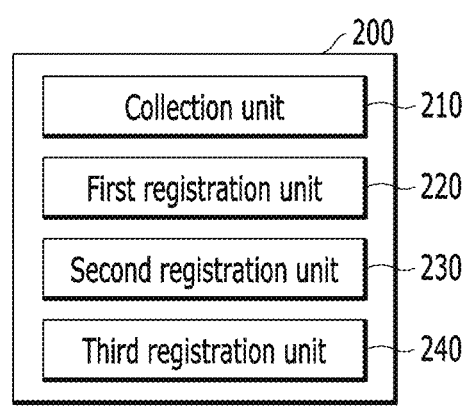
FIG. 2 is a diagram illustrating a 3D image registration providing device according to an exemplary embodiment of the present invention.

FIG. 2 is a diagram illustrating a 3D image registration providing device according to an exemplary embodiment of the present invention.

As illustrated in FIG. 2, the 3D image registration providing device 200 includes a collection unit 210, a first registration unit 220, a second registration unit 230, and a third registration unit 240.

First, the collection unit 210 acquires 3D depth data of a part to be registered, a color image of a registration body, and 3D depth data of the registration body from the depth recognition camera 100 during the surgery. The collection unit 210 acquires three-dimensional position information of a positioning tool mounted on the registration body from the positioning device 300 during the surgery.

Further, the collection unit 210 may collect pre-stored 3D surface data of a part to be registered and relative position information of a landmark from an interlinked database 400.

Next, the first registration unit 220 extracts 3D surface data of the part to be registered from the pre-stored 3D medical image of the patient and performs surface registration of the 3D depth data collected from the depth recognition camera.

The first registration unit 220 registers the 3D medical image coordinate system space and the depth recognition camera coordinate system space by means of the surface registration and generates a conversion equation.

In this case, the first registration unit 220 receives a 3D medical image stored in the database 400 before the surgery and converts the 3D medical image into 3D surface data to store the 3D surface data in the database 400 again.

Next, the second registration unit 230 extracts a color image and 3D depth data of the registration body from the image of the registration body. The second registration unit 230 deducts camera reference three-dimensional coordinates of the landmark based on the color image and the 3D depth data of the registration body.

Further, the second registration unit 230 converts the pre-stored relative position information of the landmark based on the three-dimensional coordinates of the positioning tool collected during the surgery to generate positioning device reference coordinates of the landmark.

In other words, the second registration unit 230 registers the extracted camera reference three-dimensional coordinates of the landmark and the positioning device reference coordinates of the landmark to register the depth recognition camera coordinate system space and the positioning device coordinate system space and generate a conversion equation thereof.

Next, the third registration unit 240 may perform final registration of the 3D medical image coordinate system space and the positioning device coordinate system space by the registration converting equations generated in the first registration unit 220 and the second registration unit 230.

The third registration unit 240 may store the final registration data in the interlinked database 400 during the surgery.

In the meantime, the 3D image registration providing device 200 may be a server, a terminal, or a combination thereof.

The terminal collectively refers to a device which includes a memory and a processor to have a computational processing capability. For example, examples of the terminal may be personal computers, handheld computers, personal digital assistants (PDA), mobile phones, smart devices, tablets, and the like.

The server may include a memory in which a plurality of modules is stored, a processor which is connected to the memory, responds to the plurality of modules, and processes service information which is provided to the terminal or action information which controls the service information, a communication unit, and a user interface (UI) display unit.

The memory is a device which stores information and may include various types of memories including non-volatile memories, such as a high speed random access memory, a magnetic disk storage device, a flash memory device, and other non-volatile solid-state memory devices.

The communication unit transmits and receives the service information or the action information to and from the terminal in real time.

The UI display unit outputs the service information or the action information of the device in real time. The UI display unit may be an independent device which directly or indirectly outputs or displays the UI or a part of the device.

Hereinafter, a process of registering a medical image by the 3D image registration providing device will be described in detail with reference to FIG. 3.

Figure 3:
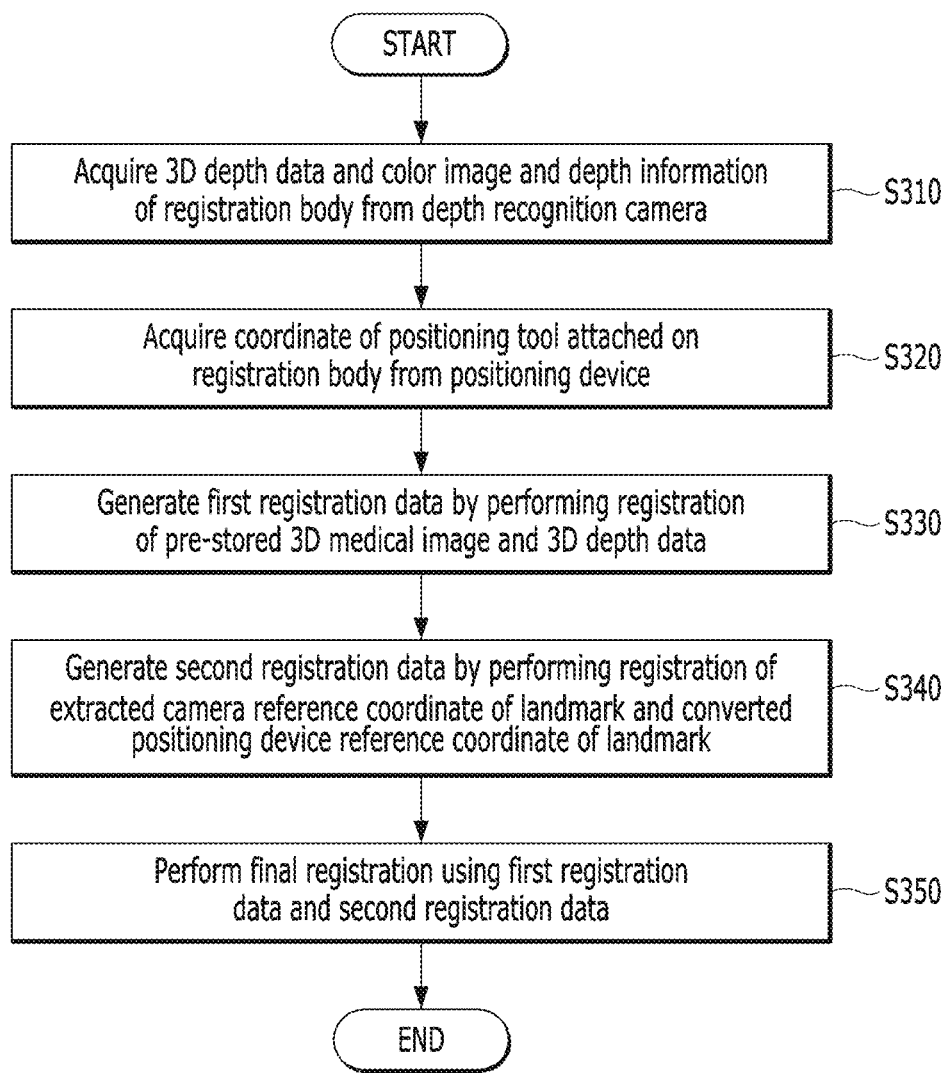
FIG. 3 is a flowchart illustrating a process of registering a 3D image by a 3D image registration providing device according to an exemplary embodiment of the present invention.

FIG. 3 is a flowchart illustrating a process of registering a 3D image by a 3D image registration providing device according to an exemplary embodiment of the present invention.

First, a 3D image registration providing method according to an exemplary embodiment of the present invention may be divided into a process before the surgery and a process after the surgery.

Here, "before surgery" indicates a time from a time when the patient receives a medical treatment for surgery to a time when the patient enters an operating room to get the surgery and "during the surgery" indicates a time from a time when the patient enters the operating room to a time when the patient moves out of the operating room after the surgery is finished.

A 3D medical image captured before the surgery according to the medical treatment record of the patient is stored in the database 400 and the 3D image registration providing device 200 may receive the 3D medical image from the database 400.

The 3D image registration providing device 200 may extract a part to be registered from the 3D medical image before the surgery and automatically or manually generate 3D surface data for the extracted part to be registered. The generated 3D surface data may be stored in the database 400 so as to correspond to the 3D medical image of the patient.

Further, after manufacturing a registration body to which a positioning tool is attached, with a plurality of landmarks for registration, before the surgery, relative position information of the landmark is extracted from the positioning tool with reference to the positioning tool to be stored in the database 400.

Hereinafter, a process of registering a coordinate system of the 3D medical image and a coordinate system of the positioning device to be matched in real time by means of the 3D image registration providing device 200 in an operating room during the surgery will be described in detail.

As illustrated in FIG. 3, the 3D image registration providing device 200 acquires 3D depth data of a part to be registered, a color image of the registration body, and 3D depth data of the registration body from the depth recognition camera 100 (S310).

The 3D image registration providing device 200 receives 3D depth data obtained by capturing a portion to be operated of the patient lying for the surgery from the depth recognition camera 100 installed at one side of the operating room. The 3D image registration providing device 200 may collect images obtained by capturing a registration body disposed in the operating room and receive the color image of the registration body and the 3D depth data of the registration body therethrough.

Next, the 3D image registration providing device 200 acquires three-dimensional coordinates of the positioning tool mounted on the registration body from the positioning device 300 (S320).

In this case, when the 3D image registration providing device 200 captures the registration body during the surgery, the three-dimensional coordinates of the positioning tool may be acquired in a state that the registration body is separately disposed so as not to be in contact, without attaching the registration body to a portion to be operated of the patient or near the portion to be operated as done in the related art.

Next, the 3D image registration providing device 200 performs surface registration of the pre-stored 3D medical image and 3D depth data to generate first registration data (S330).

Here, the first registration data includes a conversion equation to match the 3D medical image coordinate system and the depth recognition camera coordinate system.

Hereinafter, a process of generating 3D image data by the 3D image registration providing device 200 will be described in detail with reference to FIG. 4.

Figure 4:
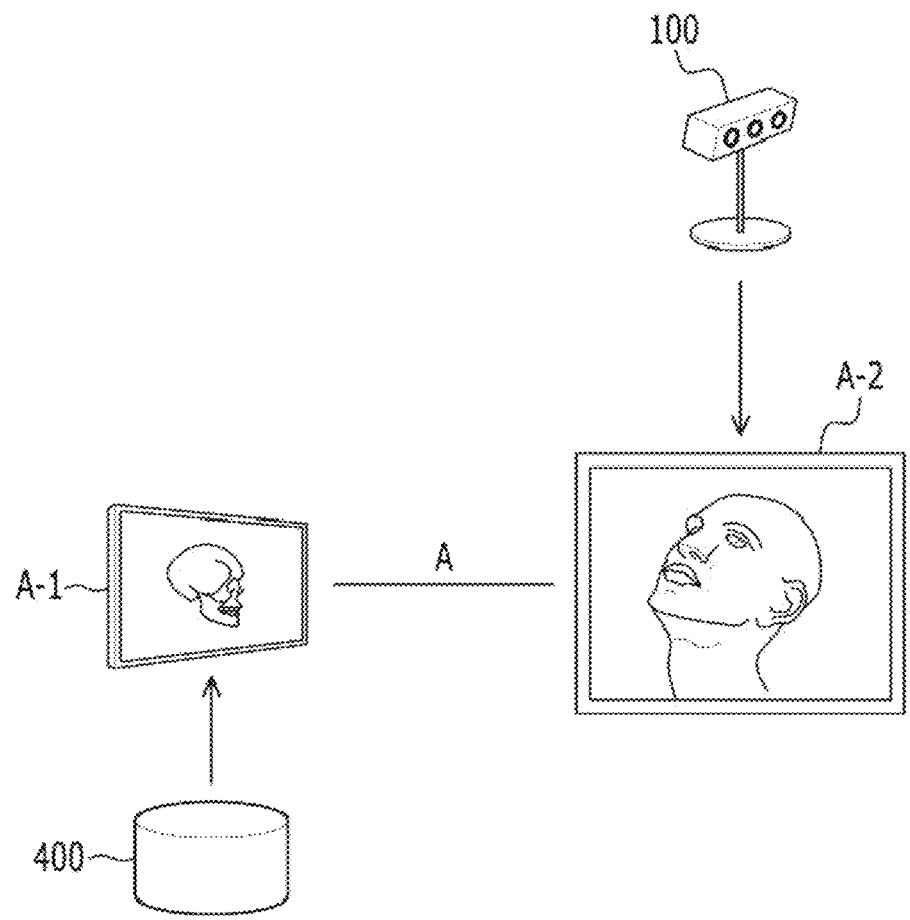
FIG. 4 is a view for explaining a process of performing registration by a first registration unit according to an exemplary embodiment of the present invention.

FIG. 4 is a view for explaining a process of registering medical images according to an exemplary embodiment of the present invention.

As illustrated in FIG. 4, the 3D image registration providing device 200 is connected to an interlinked database 400 to collect pre-stored 3D surface data A-1 of a registration portion and may convert the 3D depth data acquired in the step S310 into 3D scan data A-2.

The 3D image registration providing device 200 registers (A) the 3D surface data A-1 of the registration portion and the 3D scan data A-2 by means of at least two steps to match the 3D medical image coordinate system and the depth recognition camera coordinate system.

First, the 3D image registration providing device 200 may register the 3D surface data A-1 of the registration portion and the 3D scan data A-2 through an SAC-IA algorithm to generate the first registration data. Here, the SAC-IA algorithm is an algorithm which performs surface registration and has an advantage in that the registration result is less affected by an initial position even though the accuracy is not so high.

Accordingly, when the 3D surface data A-1 of the registration portion and the 3D scan data A-2 are registered, even though positions of corresponding points are different from each other, the 3D image registration providing device 200 may use the SAC-IA algorithm to effectively register the data.

When the 3D image registration providing device 200 generates surface registration data by means of the surface registration, the 3D image registration providing device 200 may apply the surface registration data and the 3D surface data to the ICP algorithm for the purpose of highly precise registration to register the 3D medical image coordinate system space and the depth recognition camera coordinate system space.

In other words, the 3D image registration providing device 200 applies the SAC-IA algorithm and the ICP algorithm to both 3D surface data to determine conversion between the 3D medical image coordinate system CT and the depth recognition camera coordinate system CD.

The 3D image registration providing device 200 registers the 3D medical image of the patient and the 3D surface data of the operating room so as to accurately identify the medical image information from the 3D surface data captured in the operating room during the surgery by the step-by-step registration as described above.

Next, the 3D image registration providing device 200 performs registration of the extracted camera reference three-dimensional coordinates of the landmark and the converted positioning device reference coordinates of the landmark to generate second registration data (S340).

Here, the second registration data includes a conversion equation to match the depth recognition camera coordinate system and the positioning device coordinate system.

The 3D image registration providing device 200 may perform the image processing using the color image extracted from the image of the registration body and the 3D depth data of the registration body acquired in step S310.

In this case, in order to easily extract landmarks attached to the registration body, the landmarks attached to the registration body are manufactured with different colors so that the image registration providing device 200 may extract two-dimensional coordinates of the landmarks by performing image processing on the color images. The 3D image registration providing device 200 may generate camera reference three-dimensional coordinates of the landmark using the 3D depth data of the registration body corresponding to the two-dimensional coordinates.

Hereinafter, a process of matching a depth recognition camera coordinate system and a positioning device coordinate system by the 3D image registration providing device 200 will be described in detail with reference to FIG. 5.

Figure 5:
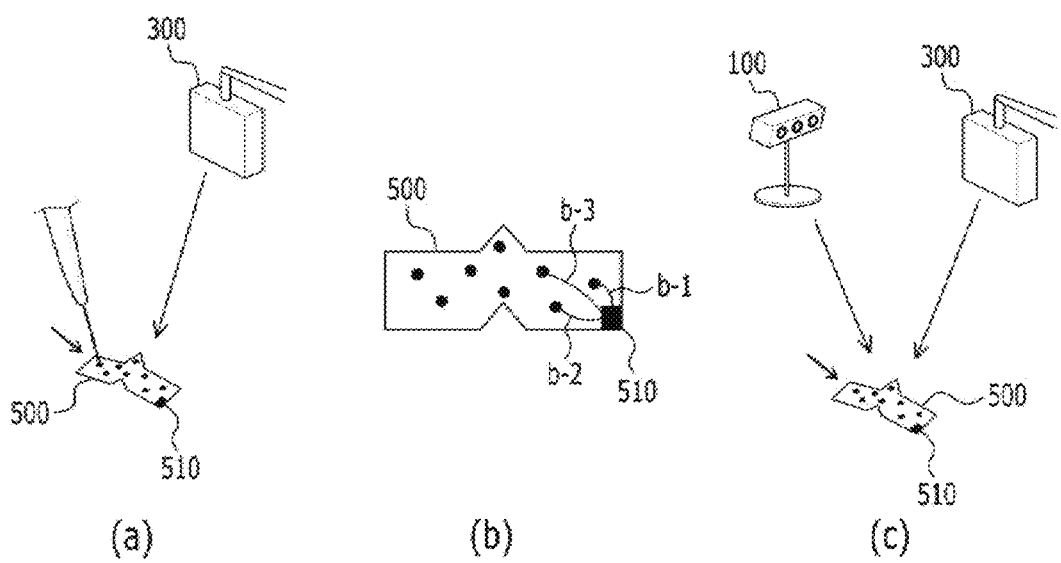
FIG. 5 is a view for explaining a process of performing registration by a second registration unit according to an exemplary embodiment of the present invention.

FIG. 5 is a view for explaining a process of performing registration by a second registration unit according to an exemplary embodiment of the present invention.

FIG. 5A is an exemplary diagram of measuring relative position information of a landmark in a circumstance before surgery, FIG. 5B is an exemplary diagram for explaining relative position information of the landmark measured before surgery, and FIG. 5C is an exemplary diagram of extracting a camera reference three-dimensional coordinate of a landmark and a positioning device reference coordinate of the landmark in a circumstance during surgery.

First, as illustrated in FIG. 5A, the 3D image registration providing device 200 may measure a three-dimensional position of the landmark of the registration body 500 by the positioning device 300 before surgery. In other words, when a tool sensor which is interlinked with the positioning device 300 is in contact with the landmark of the registration body 500, the 3D image registration providing device 200 automatically extracts the position of the corresponding landmark with the positioning tool 510 as an origin point.

Therefore, the 3D image registration providing device 200 may extract a coordinate of the landmark in the registration body 500 with reference to the positioning tool 510 of the registration body before surgery.

Further, as illustrated in FIG. 5B, the 3D image registration providing device 200 may separately store relative position information b-1, b-2, b-3, . . . , b-n which are respective distances of the landmark from the three-dimensional coordinates of the positioning tool 510. The relative position information b-1, b-2, b-2, . . . , b-n of the landmark is stored in the database 400 and is provided to the 3D image registration providing device 200 during the surgery.

When the 3D image registration providing device 200 performs image processing on the color image based on color information different from the color of the registration body 500 in the color image collected in step S310 to extract the two-dimensional position, the 3D image registration providing device 200 may deduct camera reference three-dimensional coordinate ($T_{CD}^{RB}$) of the landmark using the extracted two-dimensional position of the landmark and the 3D depth data of the registration body.

Further, the 3D image registration providing device 200 collects the three-dimensional coordinates of the positioning tool 510 in the registration body 500 with reference to the positioning tool 510 of the registration body acquired from the positioning device 300 during the surgery.

By doing this, the 3D image registration providing device 200 applies the pre-stored relative position information b-1, b-2, b-3, . . . , b-n of the landmark to the three-dimensional coordinates of the positioning tool 510 collected during the surgery to automatically convert ($T_{TR}^{RB}$).

In other words, the 3D image registration providing device 200 may convert the relative position information measured before surgery of the landmark with the positioning tool 510 as an original point into a positioning device reference coordinate collected during the surgery of the landmark with the positioning tool 510 as an original point. In that case, the 3D image registration providing device 200 performs the registration ($T_{TR}^{CD}=(T_{CD}^{RB})^{-1}T_{TR}^{RB}$) by performing one by one point to point matching on the camera reference three-dimensional coordinate ($T_{CD}^{RB}$) of the landmark and the positioning device reference coordinate of the landmark ($T_{TR}^{RB}$).

As described above, the 3D image registration providing device 200 performs point to point matching registration in real time to match the positioning device coordinate system space and the depth recognition camera coordinate system.

Next, the 3D image registration providing device 200 may perform final registration using the first registration data and the second registration data (S350).

In other words, the 3D image registration providing device 200 may match the 3D medical image coordinate system space and the positioning device coordinate system space based on previously performed two registration.

In order to register the 3D medical image data coordinate system and the positioning device coordinate system, the 3D image registration providing device 200 registers first registration data ($T_{CD}^{CT}$) in the step S330 and the second registration data ($T_{TR}^{CD}$) in the step S340, in real time.

Accordingly, the 3D image registration providing device 200 may generate a final registration image ($T_{TR}^{CT}$) as indicated in the following Equation 1.

$$T_{TR}^{CT}=T_{CD}^{CT}T_{TR}^{CD}=T_{CD}^{CT}(T_{CD}^{RB})^{-1}T_{TR}^{RB} \quad \text{[Equation 1]}$$

In the meantime, when a reference tracking tool 600 is attached to a part of a body of the patient during the surgery, the 3D image registration providing device 200 may convert a coordinate tracked by the positioning device 300 into a reference tracking tool coordinate system.

Hereinafter, a process of compensating for a movement of the patient in a final registration image by the 3D image registration providing device 200 will be described in detail with reference to FIG. 6.

Figure 6:
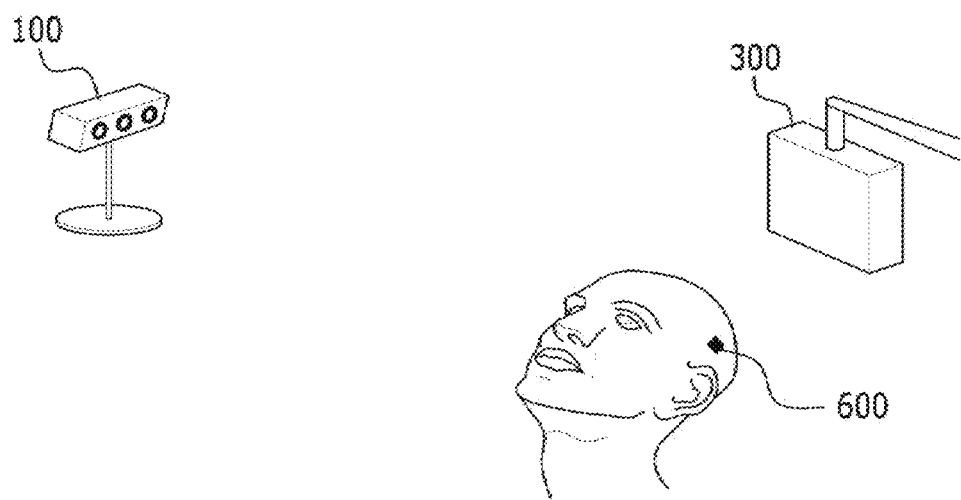
FIG. 6 is a view for explaining a process of applying a reference tracking tool coordinate system according to an exemplary embodiment of the present invention.

FIG. 6 is a view for explaining a process of applying a reference tracking tool coordinate system according to an exemplary embodiment of the present invention.

As illustrated in FIG. 6, the reference tracking tool 600 is attached to a part of a body of the patient during the surgery to more quickly and accurately detect a movement of the patient.

Accordingly, the 3D image registration providing device 200 may extract a three-dimensional coordinate with reference to the reference tracking tool 600 immediately before the surgery and convert a coordinate tracked by the positioning device 300 into a reference tracking tool coordinate system in advance.

The 3D image registration providing device 200 may apply final registration data which is a registration result of the 3D image data and the three-dimensional coordinate of the landmark to a reference tracking tool coordinate system RP.

Accordingly, the 3D image registration providing device 200 may perform final registration ($T_{RP}^{CT}$) for compensating for a movement of the patient, as indicated in the following Equation 2.

$$T_{RP}^{CT}=T_{TR}^{CT}(T_{TR}^{RP})^{-1} \quad \text{[Equation 2]}$$

In the meantime, in the 3D image registration providing device 200, the order of the step S310 of acquiring data from the depth recognition camera 100 and the step S320 of acquiring data from the positioning device 300 is not fixed so that the step S320 may be performed earlier than the step S310 or simultaneously performed with the step S310 depending on the circumstance.

Similarly, as for the order of the step S330 and the step S340, the step S330 may be performed earlier than the step S340 or simultaneously performed with the step S340 depending on the circumstance.

A program for executing a method according to an exemplary embodiment of the present invention may be recorded in a computer readable recording medium.

The computer readable medium may include solely a program command, a data file, and a data structure or a combination thereof. The medium may be specifically designed or constructed for the present disclosure or known to those skilled in the art of a computer software to be used. Examples of the computer readable recording medium include magnetic media such as a hard disk, a floppy disk, or a magnetic tape, optical recording media such as a CD-ROM or a DVD, magneto-optical media such as a floptical disk, and a hardware device which is specifically configured to store and execute the program command such as a ROM, a RAM, and a flash memory. Here, the medium may be a transmission medium such as optical or metal wire or a waveguide including a carrier wave which transmits a signal specifying program commands, data structures, or the like. Examples of the program command include not only a machine language code which is created by a compiler but also a high-level language code which may be executed by a computer using an interpreter and the like.

Although the exemplary embodiment of the present disclosure has been described in detail, the scope of the present disclosure is not limited to the disclosed embodiments, but, on the contrary, is intended to cover various modifications and equivalent arrangements included within the spirit and scope of the appended claims.

The invention claimed is:

1. A 3D image registration providing device, comprising:
a collection unit configured to acquire 3D depth data of a part to be registered and an image of a registration body from a depth recognition camera and acquire three-dimensional coordinates of a positioning tool mounted on the registration body from a positioning device;
a first registration unit configured to perform surface registration of a pre-stored 3D medical image of a patient and the 3D depth data;
a second registration unit configured to extract camera reference three-dimensional coordinates of a landmark attached to the registration body from the image of the registration body and convert pre-stored relative position information of the landmark with reference to the three-dimensional coordinates of the positioning tool, so as to perform registration of the camera reference three-dimensional coordinates of the landmark and the converted position information of the landmark; and
a third registration unit configured to perform final registration by using results of registration performed by the first registration unit and the second registration unit,
wherein the first registration unit extracts a part to be registered from the 3D medical image acquired before surgery as 3D surface data and converts the 3D depth data of the patient collected during the surgery into 3D scan data to perform surface registration between the 3D scan data and the 3D scan data.

2. The 3D image registration providing device of claim 1, wherein the first registration unit performs surface registration by means of an SAC-IA algorithm to generate surface registration data and applies the surface registration data and the 3D surface data to a precise registration ICP algorithm to generate first registration data in which a 3D medical image coordinate system and a depth recognition camera coordinate system match.

3. The 3D image registration providing device of claim 1, wherein in the registration body, the positioning tool is mounted and the landmark having a different color from the registration body is attached thereto, and a storing unit which stores relative position information of the landmark measured with reference to the positioning tool before surgery is further provided.

4. The 3D image registration providing device of claim 3, wherein the second registration unit converts pre-stored relative position information of the landmark with reference to the three-dimensional coordinates of the positioning tool collected during the surgery to generate positioning device reference coordinates of the landmark.

5. The 3D image registration providing device of claim 4, wherein the second registration unit extracts a color image of the registration body and 3D depth data of the registration body from the image of the registration body and deducts the camera reference three-dimensional coordinates of the landmark by means of a two-dimensional position of the landmark deducted using different color information from the color image and the 3D depth data of the registration body.

6. The 3D image registration providing device of claim 5, wherein the second registration unit generates second registration data to match the depth recognition camera coordinate system and the positioning device coordinate system by means of one-by-one point-to-point registration between the positioning device reference coordinates of the landmark and the camera reference three-dimensional coordinates of the landmark.

7. The 3D image registration providing device of claim 2, wherein the third registration unit registers the first registration data and the second registration data to match the coordinate system of the 3D medical image and the coordinate system of the positioning device.

8. The 3D image registration providing device of claim 7, further comprising:
a reference tracking coordinate unit which attaches a reference tracking tool to a part of a body of the patient during surgery and converts a coordinate tracked by the positioning device into a reference tracking tool coordinate system.

9. The 3D image registration providing device of claim 8, wherein the third registration unit converts data obtained by performing final registration into the reference tracking tool coordinate system.

10. A registration method of a 3D image registration providing device, the method comprising:
acquiring 3D depth data of a part to be registered and an image of a registration body from a depth recognition camera and acquiring three-dimensional coordinates of a positioning tool mounted on the registration body from a positioning device;
generating first registration data by performing registration of a 3D medical image of a patient stored in advance before surgery and the 3D depth data;
generating second registration data by extracting camera reference three-dimensional coordinates of a landmark attached to the registration body from the image of the registration body and converting pre-stored relative position information of the landmark with reference to the three-dimensional coordinates of the positioning tool, so as to perform registration of camera reference three-dimensional coordinates of the landmark and the converted position information of the landmark; and
performing final registration by using the first registration data and the second registration data,
wherein the generating of first registration data includes:

extracting a part to be registered medical image acquired before surgeryas 3D surface data;

converting the 3D depth data of the patient collected during the surgery into 3D scan data;

generating surface registration data by performing surface registration between the 3D surface data and the 3D scan data; and generating first registration data in which a 3D medical image coordinate system and a depth recognition camera coordinate system match by applying the surface registration data and the 3D surface data to a precise registration ICP algorithm.

11. The registration method of claim 10, wherein in the registration body, the positioning tool is mounted and the landmark having a different color from the registration body is attached thereto, and a storing unit which stores relative position information of the landmark measured with reference to the positioning tool before surgery is further provided.

12. The registration method of claim 11, wherein, by the second registration unit, pre-stored relative position information of the landmark is converted with reference to the three-dimensional coordinates of the positioning tool collected during the surgery to generate positioning device reference coordinates of the landmark.

13. The registration method of claim 12, wherein the second registration unit includes:

extracting a color image of the registration body and 3D depth data of the registration body from an image of the registration body;

deducting camera reference three-dimensional coordinates of the landmark by means of a two-dimensional position of the landmark deducted using different color information in the color image and the 3D depth data of the registration body; and generating second registration data to match a depth recognition camera coordinate system and a positioning device coordinate system by means of one-by-one point-to-point registration between the positioning device reference coordinates of the landmark and the camera reference three-dimensional coordinates of the landmark.

14. The registration method of claim 10, wherein in the performing of final registration, the first registration data and the second registration data are registered to match the coordinate system of the 3D medical image and the coordinate system of the positioning device.

15. The registration method of claim 14, further comprising:

attaching a reference tracking tool to a part of a body of the patient during surgery and converting a coordinate tracked by the positioning device into a reference tracking tool coordinate system.

16. The registration method of claim 15, wherein in the performing of final registration, data obtained by performing the final registration is converted into the reference tracking tool coordinate system.

17. A 3D image registration providing device, comprising:

a collection unit configured to acquire 3D depth data of a part to be registered and an image of a registration body from a depth recognition camera and acquire three-dimensional coordinates of a positioning tool mounted on the registration body from a positioning device;

a first registration unit configured to perform surface registration of a pre-stored 3D medical image of a patient and the 3D depth data;

a second registration unit configured to extract camera reference three-dimensional coordinates of a landmark attached to the registration body from the image of the registration body and convert pre-stored relative position information of the landmark with reference to the three-dimensional coordinates of the positioning tool, so as to perform registration of the camera reference three-dimensional coordinates of the landmark and the converted position information of the landmark; and a third registration unit configured to perform final registration by using results of registration performed by the first registration unit and the second registration unit, wherein in the registration body, the positioning tool is mounted and the landmark having a different color from the registration body is attached thereto, and a storing unit which stores relative position information of the landmark measured with reference to the positioning tool before surgery is further provided.

18. The 3D image registration providing device of claim 17, wherein the second registration unit converts pre-stored relative position information of the landmark with reference to the three-dimensional coordinates of the positioning tool collected during the surgery to generate positioning device reference coordinates of the landmark.

19. The 3D image registration providing device of claim 18, wherein the second registration unit extracts a color image of the registration body and 3D depth data of the registration body from the image of the registration body and deducts the camera reference three-dimensional coordinates of the landmark by means of a two-dimensional position of the landmark deducted using different color information from the color image and the 3D depth data of the registration body.

20. The 3D image registration providing device of claim 19, wherein the second registration unit generates second registration data to match the depth recognition camera coordinate system and the positioning device coordinate system by means of one-by-one point-to-point registration between the positioning device reference coordinates of the landmark and the camera reference three-dimensional coordinates of the landmark.

* * * * *